United States Patent [19]

Zimmerman

[11] 4,318,401

[45] Mar. 9, 1982

[54] PERCUTANEOUS VASCULAR ACCESS PORTAL AND CATHETER

[75] Inventor: Clarence E. Zimmerman, Cambridge, Mass.

[73] Assignee: President and Fellows of Harvard College, Cambridge, Mass.

[21] Appl. No.: 143,468

[22] Filed: Apr. 24, 1980

[51] Int. Cl.³ .............................................. A61M 5/00
[52] U.S. Cl. ................................ 128/214 R; 128/347; 128/348
[58] Field of Search ............. 128/214 R, 214.2, 214.4, 128/334, 347, 348, 207.14, 305.3; 3/1

[56] References Cited

U.S. PATENT DOCUMENTS

| | | | |
|---|---|---|---|
| 3,547,119 | 12/1970 | Hall ..................................... | 128/348 |
| 3,613,684 | 10/1971 | Sheridan ............................. | 128/347 |
| 3,713,441 | 1/1973 | Thomas .......................... | 128/214 R |
| 3,815,577 | 6/1974 | Bucalo ......................................... | 3/1 |
| 3,818,511 | 6/1974 | Goldberg et al. .................. | 128/348 |
| 3,991,756 | 11/1976 | Snyder ............................ | 128/214 R |
| 3,993,079 | 11/1976 | Gatztanondo ...................... | 128/347 |
| 4,096,860 | 6/1978 | McLaughlin ..................... | 128/214.4 |
| 4,099,528 | 7/1978 | Sorenson et al. .................... | 128/348 |
| 4,108,174 | 8/1978 | Slivenko ............................. | 128/348 |
| 4,122,858 | 10/1978 | Schiff ................................... | 128/348 |
| 4,164,221 | 8/1979 | Bentley et al. ...................... | 128/348 |
| 4,180,068 | 12/1979 | Jacobson et al. ............... | 128/214 R |
| 4,236,520 | 12/1980 | Anderson ............................ | 128/348 |
| 4,270,535 | 6/1981 | Bogue et al. ........................ | 128/347 |

OTHER PUBLICATIONS

"Tomas Femoral Shunt", Physio-Control Corp. brochure.

*Primary Examiner*—Gene Mancene
*Assistant Examiner*—John J. Wilson

[57] ABSTRACT

A percutaneous vascular access portal for implantation in a patient for an extended period of time including a cannula having a skirt at its distal end for attaching to the wall of a blood vessel and a flange at the other end to be located near the patient's skin surface and to provide a stop for catheters that are inserted therein and accurately locate their distal ends and openings in the blood vessel. The portal is provided with an obturator to block flow through the cannula when the portal is not being used, the obturator fitting snugly and sealably within the cannula and allowing for no dead space within the cannula in which blood could stagnate. Also disclosed are catheters for use with an implanted vascular access portal having elongate portions that snugly and sealably fit within the portal cannula, stops on one end of the elongate portion for contacting the portal flange, distal openings for communicating with the vessel interior when the stops contact the flange, and pointed means for puncturing the vessel wall and facilitating insertion of the catheters.

15 Claims, 9 Drawing Figures

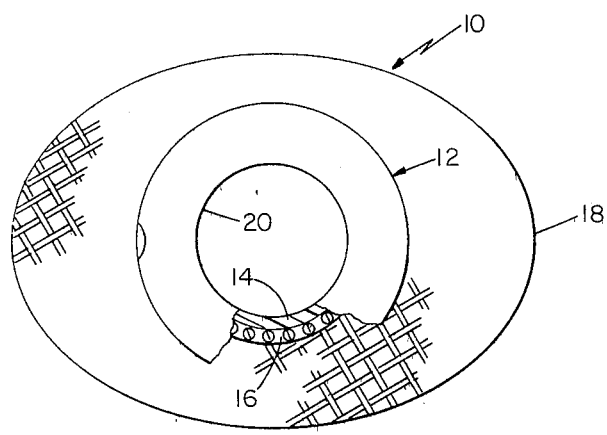
FIG 1
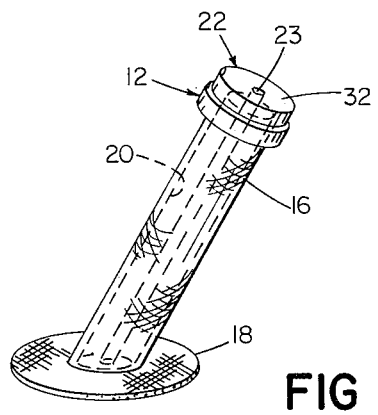
FIG 1A
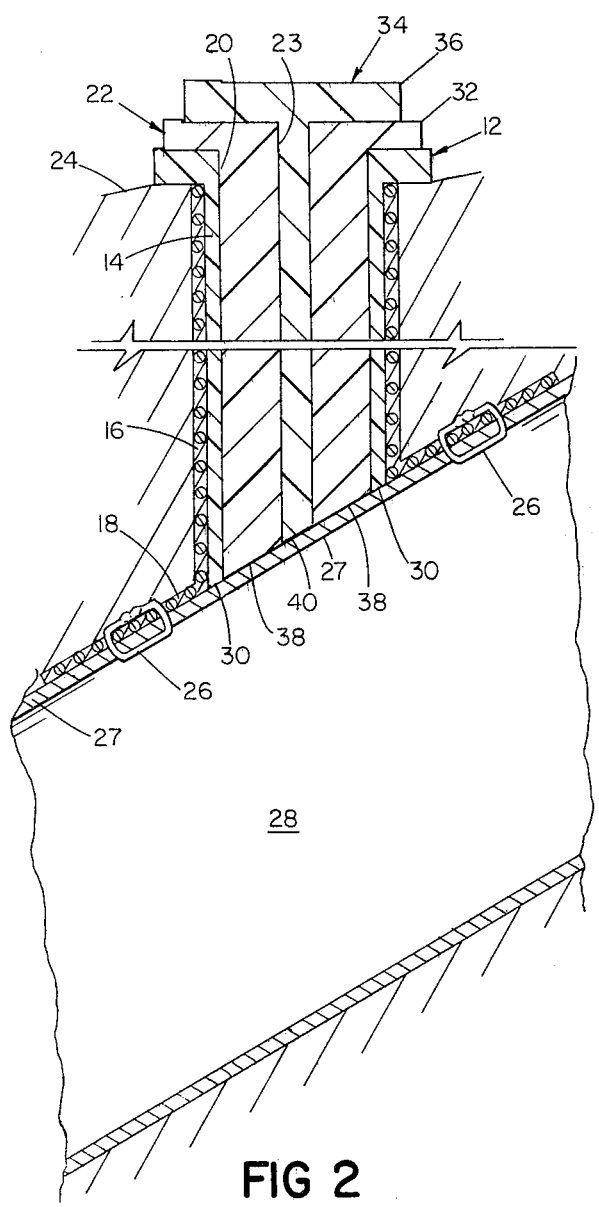
FIG 2
FIG 3
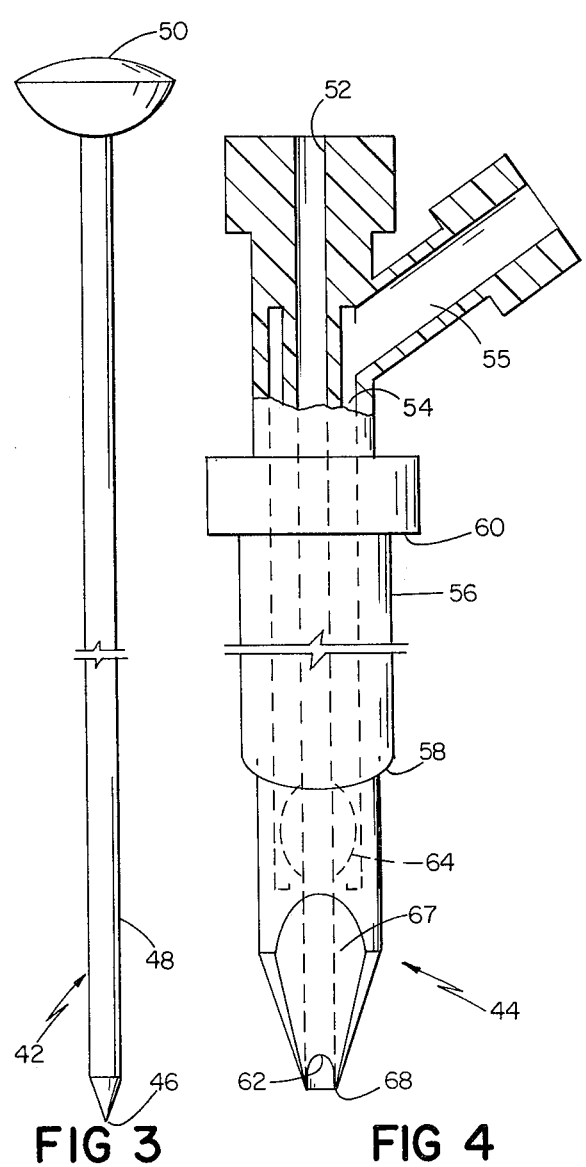
FIG 4

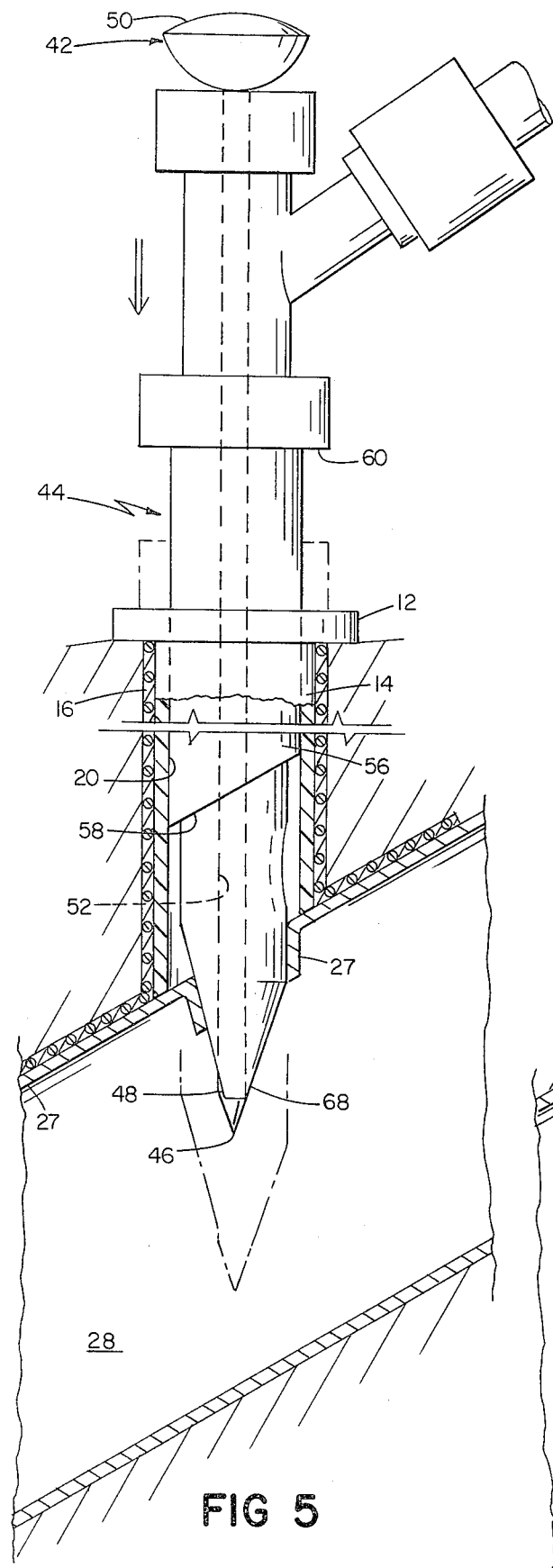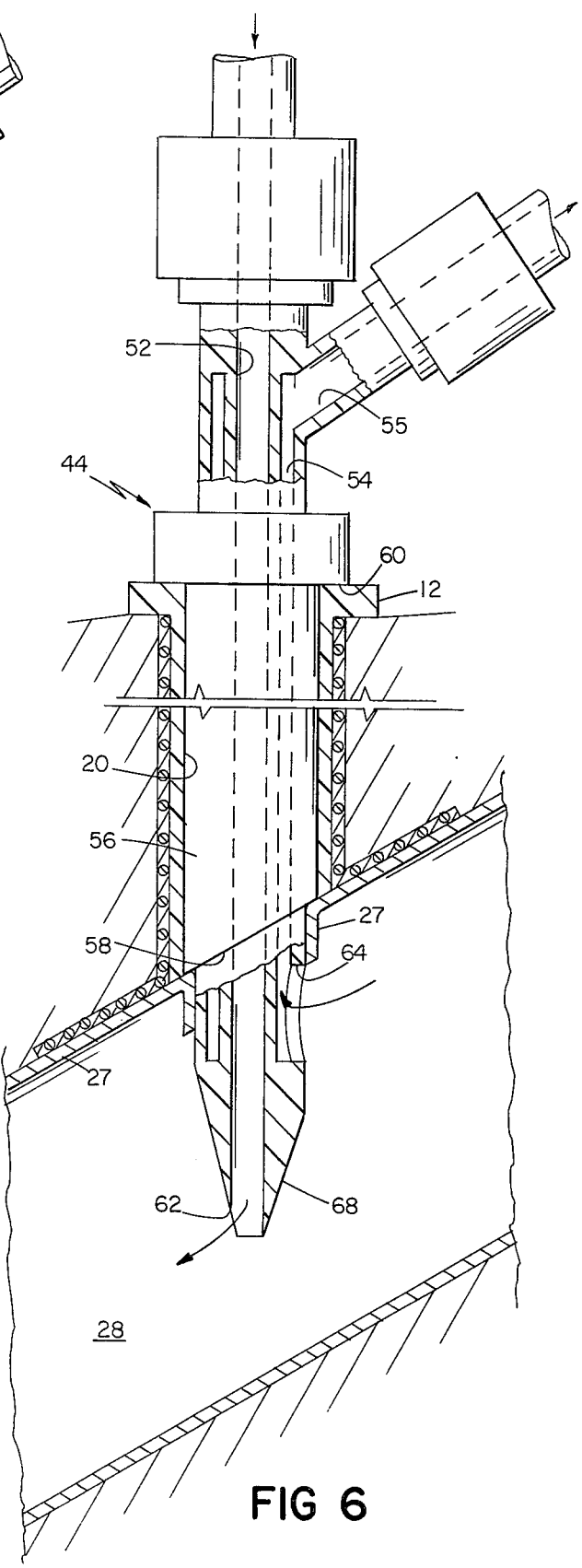

PERCUTANEOUS VASCULAR ACCESS PORTAL AND CATHETER

This invention relates to percutaneous vascular access portals and catheters for use with the same.

Chronic periodical vascular access is necessitated in a number of situations, e.g., chronic hemodialysis, intravenous infusion of chronic anti-cancer chemotherapeutic agents, etc. When a primary vascular access (e.g., A-V wrist fistula or A-V wrist Scribner shunt) has failed or is not available, secondary access surgery is performed to provide dependable and safe vascular access. One type of secondary access surgery is known as the Thomas Femoral Shunt, which involves implanting two silastic tubes, which are surrounded by Dacron velour sleeves and have skirts at the buried ends of the tubes. The skirts are attached around openings in the femoral artery and the femoral vein. The unattached ends of the tubes extend from the patient's skin and are looped when not in use and thereby provide a shunt. Synder U.S. Pat. No. 3,991,756 discloses a single needle access device, which is surgically implanted adjacent to a bypass blood vessel and has a number of openings along its length. When access to the vessels is desired, a needle having a laterally extending blade is inserted into the device, the blade makes a cut through one of the openings into the vessel wall, and the end of a catheter is then guided into the hole. When access is not desired, a silastic trocar, which is designed to completely fill the cannula interior, is inserted.

It is a major object of the invention to provide a means for chronic periodical vascular access that can be simply employed without the problems of infection or thrombosis and in which there is prompt healing of the vessel wall after use, and the development of scar tissue is avoided.

It is a further object to provide vascular access that can be used in hemodialysis through only one access portal.

It is yet another object to provide vascular access that prevents the puncturing of both walls of the blood vessels and accurately places catheter inlets and outlets within the blood vessel.

It is another object of the invention to provide a vascular access portal having no regions within which blood can stagnate during access or between accesses to avoid blood-clotting therein.

It is another object of the invention to provide a vascular access portal allowing for ease of insertion and removal of catheters and of an obturator, which blocks the portal when access is not desired.

Accordingly, the present invention provides a percutaneous vascular access portal that allows for the ease of insertion of catheters into blood vessels, avoids infection, promotes healing of the vessel wall, avoids the development of scar tissue, and avoids thrombosis. The portal comprises a cannula having a skirt at its distal end for attaching to the wall of a blood vessel and a flange at the other end to be located near the patient's skin surface and to provide a stop for catheters that are inserted therein and accurately locate their distal ends and openings in the blood vessel. The portal is provided with an obturator to block flow through the cannula when the portal is not being used, the obturator fitting snugly and sealably within the cannula and allowing for no dead space within the cannula in which blood could stagnate. In preferred embodiments the cannula is made of silastic material; the skirt is made of a mesh; the cannula is wrapped with a sleeve of a material such as polyester velour having a non-smooth surface to promote ingrowth of the patient's tissue and avoid infection; the cannula is designed to make an acute angle with the longitudinal axis of the blood vessel; and the obturator comprises inner and outer obturators, the inner obturator being snugly fit within a bore in the outer obturator.

In another aspect the invention features a catheter for use with the above-described portal. The catheter has an elongate portion that snugly and sealably fits within the portal cannula, a stop on one end of the elongate portion for contacting the portal flange, a distal opening for communicating with the vessel interior when the stop contacts the flange, and pointed means for puncturing the vessel wall and facilitating insertion of the catheter.

In a most preferred embodiment the catheter is used for hemodialysis and has two lumens therethrough for communication with the vessel interior, the distal opening for one lumen being directed away from the distal opening for the other lumen; the openings are axially displaced from one another; the two lumens are concentrically located; and the puncturing means is a metal trocar that slidable engages the center lumen.

In another embodiment the catheter has a distal opening with a cross-section identical to that of its lumen, and it has a puncturing needle slidably mounted within the lumen. In one embodiment the needle has a laterally disposed opening, and in another embodiment the needle has an axial opening with a cross section identical to that of the needle lumen.

Other objects, features and advantages will appear from the following description of particular embodiments of the invention, taken together with the drawing, in which:

FIG. 1 is a plan view, partially broken away, of a vascular access portal according to the invention;

FIG. 1a is an isometric view of said portal;

FIG. 2 is a vertical sectional view of said portal shown implanted in a patient and attached to a blood vessel;

FIG. 3 is an elevation of a puncturing element for a catheter according to the invention;

FIG. 4 is an elevation, partially broken away and in section and having its top rotated 90° relative to a bottom portion, of a two lumen said catheter for use with an access portal in accordance with the invention;

FIG. 5 is an elevation, partially broken away and in section, of said catheter during insertion into an implanted access portal;

FIG. 6 is an elevation, partially broken away and in section, of said catheter after insertion;

Figure 7:
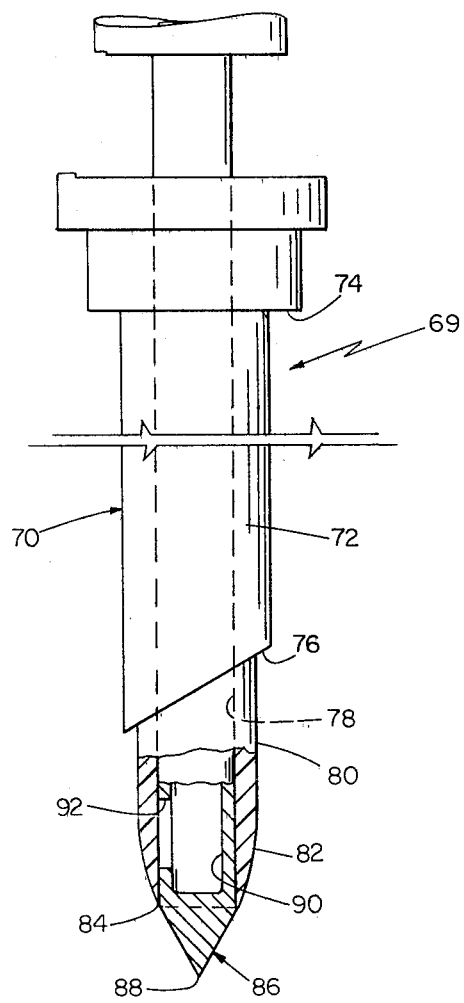
FIG. 7 is an elevation, partially broken away and in section, of another embodiment of a catheter for use with an access portal in accordance with the invention.

Referring now to the drawing, and particularly to FIGS. 1 and 2, there is shown vascular access portal 10 having radially outwardly extending flange 12 at its proximal end and cannula 14 (both made of silicon rubber), sleeve 16 (Dacron polyester velour), and radially outwardly extending skirt 18 (Dacron polyester mesh). Cannula 14 has passage 20 therethrough, and in FIG.

1a, outer plastic obturator 22, having relatively small diameter longitudinal bore 23 through it, is shown inserted therein. Obturator 22 and passage 20 are sized to provide a snug and sealable fit, and obturator 22 fills the entire region of passage 20.

In FIG. 2 portal 10 is shown implanted within a patient, flange 12 resting on or close to outer skin surface 24, skirt 18 being fastened by sutures 26 to the wall 27 of femoral vein 28, distal end surface 30 of cannula 14 resting against the outer blood vessel wall 27. The non-smooth surface of sleeve 16 promotes tissue ingrowth after implantation and avoids infection. Radially outwardly extending flanged stops 32 of plastic obturator 22 are shown contacting flange 12. Inner obturator 34 of plastic or metal is sealably fit within outer obturator 22, its head 36 resting on stop 32. When obturators 22, 34 are thus inserted, their distal end surfaces 38, 40, respectively, contact vessel wall 27 and thereby avoid dead space which could lead to blood clotting therein and eventual thrombosis of vein 28.

In use after implantation, smaller obturator 34 is removed first. Because it has a relatively small cross-section, only a small area of wall 27 is subjected to suction, minimizing possible trauma. Then large obturator 22 can be removed, its open passage 23 providing a vent to facilitate its removal without subjecting the vessel wall to distorting force.

Referring to FIGS. 3 through 6, there are shown metal or plastic trocar 42 and double-lumen plastic catheter 44 for use with portal 10. Trocar 42 has sharp conical puncturing point 46, elongate portion 48, preferably of circular cross-section, and head 50. Catheter 44 has inner flow-through lumen 52 (sized to provide a snug fit for trocar 42 when inserted therein) and outer concentric lumen 54 communicating with outlet 55. When catheter 44 is used in hemodialysis, lumen 54 and outlet 55 are connected to the inlet of the dialyzer, and lumen 52 is used to return blood from the dialyzer outlet to the blood vessel of the patient. Cylindrical portion 56 is sized to provide a snug and sealable fit within passage 20, and elliptically annular surface 58 contacts a blood vessel surface when stop 60 contacts flange 12, surface 58 being adjacent to blood vessel wall 27 in this position. Lumen 52 has distal outlet opening 62 formed by intersection of flat surface 67 with lumen 52 adjacent the tip of conical distal end 68 of catheter 44, and lumen 54 has distal inlet opening 64 through the outer wall of catheter 44. In FIG. 4 the upper portion of catheter 44 is shown rotated 90° from the lower portion. Thus, outlet 55 is in reality aligned radially with opening 64.

In FIG. 5, catheter 44 is shown during insertion with trocar 42 therein, and in FIG. 6 it is shown after insertion with trocar 42 withdrawn, in position for the flow of blood therethrough. The lower portion of catheter 44 is shown properly aligned with its upper portion, i.e., rotated 90° relative to the position shown in FIG. 4. Wall 27 is punctured during insertion by conical point 46, and conical surface 68 of catheter 44 stretches the punctured vessel wall 27 symmetrically and uniformly as it penetrates. Conical surface 68 of catheter 44 has the same angle as the surface around point 46 of trocar 42, and thus, a smooth transition is provided. Similarly, the edges around opening 62 and between conical surface 68 and flat surface 67 are machined smoothly to avoid cutting the wall 27 during insertion.

As can be seen in FIG. 6, when stop 60 contacts flange 12 both openings 62 and 64 communicate with the interior of blood vessel 28, and the distal end of catheter 44 is located near the center of the blood vessel spaced from the far wall thereof.

During dialysis, the tight fit of cylindrical portion 56 within cannula 14 prevents the leakage of blood into the port and the resultant possible thrombosis. Moreover, because of the angular and linear displacement between distal openings 62, 64, return blood flowing through the former does not mingle with blood entering the catheter through the latter, particularly when inlet 64 is facing upstream.

After dialysis, catheter 44 is removed and obturators 22, 34 are replaced in sequence, the reverse of the sequence of removal. Because the vessel wall 27 is punctured rather than cut, wall 27 tends to resume its former shape, bland healing occurs in a relatively short period of time, and scar tissue is avoided. Outer obturator 22 is first inserted into passage 20, and any blood therein flows to its center opening 23 along with any air bubbles. Inner obturator 34 is then inserted within hole 23, its smaller cross section allowing for ease of insertion and minimizing the trapping of air.

Figure 8:
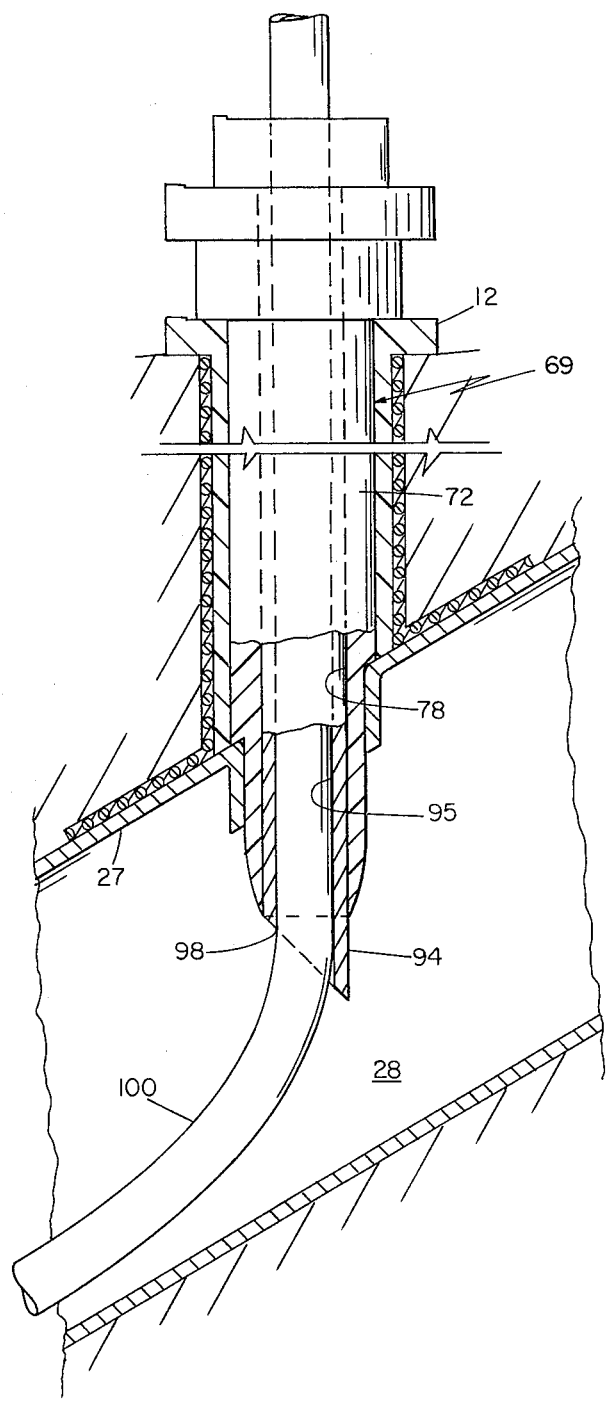
FIG. 8 is an elevation, partially broken away and in section, of still another catheter embodiment inserted in an access portal in accordance with the invention.

FIGS. 7 and 8 show another embodiment, a catheter 69 to be used for providing long-term access for infusion of drugs or central lines for intravenous feeding. Outer silicone plastic tube 70 has cylindrical portion 72, stop 74, and elliptical surface 76, which are all identical in structure and function to portions 56, 60, 58, respectively, of catheter 44. Tube 70 has central axial bore 78 passing longitudinally therethrough, and small diameter portion 80 tapering at 82 to axial opening 84 for communicating with bore 78. Metallic puncturing trocar 86 is snugly and sealably fit within passage 78 and has pointed end 88, cylindrical passage 90, and lateral opening 92 communicating with cylindrical passage 90.

In use, catheter 69 is inserted in access portal 10 with trocar 86 in the position shown in FIG. 7. After insertion trocar 86 can be axially displaced downwardly relative to tube 72 thereby causing opening 92 to communicate with the interior of blood vessel 27. Fluids can be infused into the vessel through opening 92 or samples of blood can be removed therefrom.

In FIG. 8 there is shown catheter 69 with trocar 86 removed and cannula 94 fit within tube 72. Cannula 94 has a distal opening 98 with a transverse cross-section identical to that of its longitudinal bore 95. Cannula 94 can have its upper end connected to hypodermic syringe (not shown) for sampling blood, or a flexible cather 100 can be inserted through it and used for intravenous feed and the like.

Other embodiments will be obvious to those skilled in the art. For example, the upper surface of flange 12, and stops 32 and 74, and head 36 need not be perpendicular to cannula 14, but can make an acute angle with it. If the blood vessel to be punctured is parallel to the skin surface, then skirt 26 would be parallel to these members and surface.

What is claimed is:
1. Percutaneous blood-vessel access portal for implantation in a patient for an extended period of time comprising
   a cannula having a distal end forming an acute angle with respect to the main axis of the cannula,
   a skirt secured to said cannula and extending generally radially outwardly from said distal end,
   said skirt being adapted to be secured to the wall of a blood vessel with the proximal end of said cannula extending outwardly through the skin and with the axis of said cannula forming an acute angle with the axis of said blood vessel, and a removable obturator forming a snug fit within the passage of said cannula adapted to seal said passage, the distal end of said obturator forming an acute angle with respect to the main axis of the obturator matching the angularity of the cannula distal end, said obturator having adjacent its proximal end a radially outwardly extending flange overlying the margin of said portal cannula proximal end and serving as a stop to locate the distal end of said obturator in registration with the distal end of said cannula.

2. An access portal as claimed in claim 1 including in addition a plastic sleeve having a non-smooth surface attached to the exterior surface of said cannula between said distal and proximal ends.

3. An access portal as claimed in claim 2 wherein said sleeve is polyester velour.

4. An access portal as claimed in claim 1 wherein said cannula is made of silicone plastic material.

5. An access portal as claimed in claim 4 wherein said skirt is made of polyester mesh.

6. An access portal as claimed in claim 1 wherein said acute angle is about 30°.

7. An access portal as claimed in claim 1 wherein said obturator comprises an inner and outer obturator, said inner obturator being slidably and removably mounted within a longitudinal bore of said outer obturator, said inner obturator making a snug and sealable fit in said outer obturator.

8. A double-lumen catheter for insertion into a blood vessel through an implanted access portal secured thereto, said catheter comprising a shaft forming a snug fit within said portal and having a tapered distal end and having a centrally-located axial lumen and a separate lumen parallel to the first, each lumen extending from an access opening adjacent the proximal end of said catheter to an opening adjacent its distal end, said distal opening each being located respectively at opposite sides of said distal end of said shaft, and a radially outwardly extending catheter flange secured to said shaft and spaced from its distal end in position to engage the proximal end of said access portal upon insertion of said catheter into said portal and to position the distal end of said catheter together with the adjacent lumen distal openings within said blood vessel.

9. A catheter as claimed in claim 8 comprising in addition a trocar removably inserted within said axial lumen and forming a snug fit therewith, said trocar having a conically-pointed puncturing end for piercing the wall of said blood vessel and having a radially outwardly extending trocar flange adapted to abut the proximal end of said catheter, said trocar flange being spaced from said puncturing end to position said end at the distal end of said catheter to puncture the wall of said blood vessel when said catheter and trocar are together inserted into said portal.

10. A catheter as claimed in claim 9 wherein said conically pointed end of said trocar is arranged to form an extension of said tapered end of said cather and to merge therewith when said trocar flange abuts said proximal end of said catheter.

11. A catheter as claimed in claim 8 wherein said distal openings are longitudinally spaced from each other along the longitudinal axis of said shaft.

12. A catheter as claimed in claim 8 wherein said lumens are concentrically located.

13. A method for percutaneously accessing a patient's blood vessel comprising implanting an access portal within a patient, said portal having a cannula, a skirt secured to a distal end of said cannula, and a proximal end, said skirt being sutured to a wall of said blood vessel, said proximal end extending outwardly through the skin of said patient, inserting into said cannula a catheter with a conically-pointed trocar removably mounted in and extending from a distal opening of a centrally-located axial lumen thereof, to puncture said wall, and to position said distal opening within said blood vessel, and withdrawing said trocar to allow access to said blood vessel via said lumen.

14. A kit for providing percutaneous blood-vessel access comprising (1) a portal for implantation in a patient for an extended period of time including a cannula having a distal end forming an acute angle with respect to the main axis of the cannula, a skirt secured to said cannula and extending generally radially outwardly from said distal end, said skirt being adapted to be secured to the wall of a blood vessel with the proximal end of said cannula extending outwardly through the skin and with the axis of said cannula forming an acute angle with the axis of said blood vessel, and (2) a removable obturator forming a snug fit within the pasage of said cannula adapted to seal said passage, the distal end of said obturator forming an acute angle with respect to the main axis of the obturator matching the angularity of the cannula distal end, said obturator having adjacent its proximal end a radially outwardly extending flange overlying the margin of said portal cannula proximal end and serving as a stop to locate the distal end of said obturator in registration with the distal end of said cannula, and (3) a double lumen catheter interchangeable with said obturator for insertion into a blood vessel through said portal, comprising a shaft forming a snug fit within said portal and having a tapered distal end and having a centrally-located axial lumen and a separate lumen parallel to the first, each lumen extending from an access opening adjacent the proximal end of said catheter to an opening adjacent its distal end, said distal openings each being located respectively at opposite sides of said distal end of said shaft, and a radially outwardly extending catheter flange secured to said shaft and spaced from its distal end in position to engage the proximal end of said access portal upon insertion of said catheter into said portal and to position the distal end of said catheter together with the adjacent lumen distal openings within said blood vessel.

15. A kit as claimed in claim 14 in which said obturator comprises an inner and outer obturator, said inner obturator being slidably and removably mounted within a longitudinal bore of said outer obturator, said inner obturator making a snug and sealable fit in said outer obturator.

* * * * *